United States Patent [19]

Fujisaki et al.

[11] 4,425,921
[45] Jan. 17, 1984

[54] APPARATUS FOR CHECKING PULSE AND HEART RATES

[75] Inventors: Iwao Fujisaki, Ichikawa; Shuichi Kosuge, Tama; Syuu Ogawa, Kasukabe; Kimihiko Sato, Funabashi; Toshimi Soeda, Tokyo, all of Japan

[73] Assignee: Senoh Kabushiki Kaisha, Tokyo, Japan

[21] Appl. No.: 301,122

[22] Filed: Sep. 11, 1981

[30] Foreign Application Priority Data

Jan. 19, 1981 [JP] Japan .................................. 56-5955

[51] Int. Cl.$^3$ ............................................... A61B 5/02
[52] U.S. Cl. ................................... 128/690; 128/644; 128/664; 128/700
[58] Field of Search ............................... 128/639–641, 128/644, 664–667, 687–690, 670, 671, 696, 700, 706, 710

[56] References Cited

U.S. PATENT DOCUMENTS

| | | | |
|---|---|---|---|
| 3,871,362 | 3/1975 | Dunegan | 128/666 |
| 4,026,278 | 5/1977 | Ricketts et al. | 128/644 |
| 4,108,166 | 8/1978 | Schmid | 128/710 X |
| 4,121,575 | 10/1978 | Mills et al. | 128/644 |
| 4,122,843 | 10/1978 | Zdrojkowski | 128/644 |
| 4,181,134 | 1/1980 | Mason et al. | 128/690 X |
| 4,182,346 | 1/1980 | Allison | 128/641 |
| 4,305,401 | 12/1981 | Reissmuller et al. | 128/690 |
| 4,312,358 | 1/1982 | Barney | 128/670 |
| 4,367,752 | 1/1983 | Jimenez et al. | 128/689 |

FOREIGN PATENT DOCUMENTS

| | | | |
|---|---|---|---|
| 2135019 | 1/1972 | Fed. Rep. of Germany | 128/706 |
| 2521425 | 11/1976 | Fed. Rep. of Germany | 128/666 |

OTHER PUBLICATIONS

"CT-200 Cardiotechameter" The Waters Co., Bulletin CT200/65, 10/1965.
Lee et al., "An LED-Transistor . . . ", IEEE Trans. on Bio Med. Eng., vol. 22, No. 3, pp. 248–250, May 1956.

*Primary Examiner*—Lee S. Cohen
*Attorney, Agent, or Firm*—Lowe, King, Price & Becker

[57] ABSTRACT

A small portable-type apparatus for checking pulse or heart rate of a person engaged in exercise. Therefore, the apparatus according to the present invention can be used as a pulsimeter or a cardiometer according to the state of a person in motion. The apparatus is provided with a heart sensor having a plurality of cone-shaped conductive rubber electrodes to differentially detect an electrocardiowave voltage signal generated from three different places near the heart and a pulse sensor having a matching infrared-ray emitting diode and infrared-ray receiving phototransistor to detect the light reflected from the blood flowing through capillary vessels under the finger pad. The apparatus additionally functions as a stopwatch or a timer as selected by a mode-selector switch.

5 Claims, 10 Drawing Figures

APPARATUS FOR CHECKING PULSE AND HEART RATES

BACKGROUND OF THE INVENTION

1. Field of the Invention

The present invention relates generally to an apparatus for checking pulse rate and heart rate independently by simply exchanging the heart sensor for the pulse sensor or vice versa, and more particularly to the apparatus with a heart sensor having a plurality of cone-shaped conductive rubber electrodes to differentially detect an electric cardiowave voltage signal generated from near the heart and a pulse sensor having a matching light-emitting diode and light-receiving phototransistor to detect the light reflected from the blood flowing through capillary vessels under the finger pad.

2. Description of the Prior Art

Recently, many people have taken an increasing interest in building up their physical strength or in promoting their own health, and therefore running has become more and more popular. However, in the case of a person developing his stamina or taking exercise who has no good adviser to coach him, the exerciser may be in danger of ruining his health due to excessively heavy exercise. To avoid such an unfavorable condition, there is an urgent need for a simple method of checking for a degree of exercise suitable to the user's current health conditions. One of the methods of checking the above-mentioned conditions is to check pulse rate or heart rate while the person is in motion.

The pulse rate is the number of blood surges in blood vessels generated whenever blood is fed from the heart to the blood vessels, that is, the number of pulses counted for one minute. A sensor for detecting the rate of pulse is usually attached to some portion of the body, preferably by selecting an appropriate skin site, such as fingertips or earlobes, where there are many capillary vessels under the skin.

For detecting the rate of pulse, a method has been adopted in which light is transmitted from a light emitting element to the capillary vessels near which the sensor is attached and the reflected light is next detected by a light-receiving element to detect the pulsatory motion of the blood.

In such a method as described above, however, there exists the factor of the weight of blood itself in addition to the pulsatory motion caused by the heart. When motion or vibration occurs within the body due to heavy exercise, this motion can cause the blood vessels to produce the same pulsatory motion as in the pulse, thus making it impossible to check the rate of pulse accurately when the person is in motion or in vigorous exercise.

In addition to the above problem, the blood vessels near the skin of the fingertips or earlobes are extremely sensitive to external temperature. When cooled the skin shrinks to prevent heat from being emitted; the blood vessels themselves also shrink to prevent heat from being transmitted; the blood vessels move away from the skin, thus making it impossible to detect the pulsatory motion of the blood reliably.

Furthermore, there is some difficulty in that when the body is exposed directly to the sun, direct rays of the sun are detected by the light-receiving element after passing through the skin, thus disturbing the accurate detection of the pulse rate, especially when a faint pulse rate is required to be checked.

Since there are many unstable factors when measuring the rate of pulse as already described hereinabove, there has been proposed a method of checking the number of heartbeats themselves, that is, the source of pulse.

The heart serves as a pump to feed blood throughout the body, and a kind of small current termed electrocardiowave passes through the heart whenever the heart beats. Therefore, the number of heartbeats is usually measured depending upon the number of these electrocardiowaves counted during one minute.

Since the electrocardiowave is not subject to the interfering influences of body vibration, change in external temperature, direct rays of the sun etc., it is possible to check the state of heartbeats more accurately. To detect such a small current as the cardiowave signal, however, it is necessary to attach the sensor near the heart, particularly in direct contact with the skin. Therefore, the person to be checked must be at least partially naked, which can be rather troublesome.

That is to say, since the described methods of measuring pulse rate and heart rate each have some merits and drawbacks, it is desirable to provide a simple single measuring unit which can check pulse rate or heart rate independently according to the time, place, and necessity, including the case of a person in motion.

In a conventional heart sensor, a plurality of electrodes are attached on the skin separately by using an adhesive tape, and connected to the measurement unit by using a plurality of long lead wires. Accordingly, it has been very troublesome to attach and detach the electrodes to and from the skin, and additionally there has been relatively great error caused by the positioning of the electrodes.

To overcome this problem, there exists a method of temporarily arranging the electrodes on a belt by using an adhesive tape. However, since the electrodes are simply arranged on a flexible belt and the lead wires are simply provided separately from the belt, the electrodes are liable to be moved while the person to be checked is in motion or engaged in exercise, thus producing unfavorable noise to interfere with accurate measurement of electrocardiowave signal.

Further, in the case of pulse sensors, there exist various kinds such as a simple sensor attached to the skin with adhesive tape, a clip-type sensor, a non-flexible plastic ring-shaped sensor, etc. However, these conventional sensors do not provide for easy attachment to the skin, elimination of perspiration, and comfort.

SUMMARY OF THE INVENTION

With these problems in mind therefore, it is the primary object of the present invention to provide in apparatus for checking pulse rate or heart rate, that is, usable as a pulsimeter or a cardiometer by replacing one sensor with the other sensor employable by a person in motion or exercising, for more accurate measurement of pulse rate or heart rate.

It is another object of the present invention to provide a heart sensor for detecting heart rate and a pulse sensor for detecting pulse rate, both easy to handle and accurate when the person to be checked is in motion or engaged in exercise, with due consideration of perspiration and comfort.

To achieve the above-mentioned object, the apparatus for checking pulse and heart rate according to the present invention comprises a heart sensor for detecting an electrocardiowave signal, a pulse sensor for detecting pulse, an analog switch for connecting the two sensors independently, a microcomputer for calculating heart rate or pulse rate, and an indicator unit.

Further, the heart sensor according to the present invention comprises a flexible silicon rubber strap having a number of holes, three circular-cone-shaped, flexible, conductive rubber electrodes, and a pair of cloth belts with a buckle and clip.

Furthermore, the pulse sensor according to the present invention comprises a flexible, silicon-rubber, roughly-cylindrical ring having a horseshoe-shaped cross-section with bulbous lips at either end thereof bridged by a sensor unit including a matching infrared-ray emitting diode and phototransistor.

BRIEF DESCRIPTION OF THE DRAWINGS

The features and advantages of the apparatus for checking pulse rate and heart rate according to the present invention will be more clearly appreciated from the following description taken in conjunction with the accompanying drawings in which like reference numerals designate corresponding elements and in which.

DETAILED DESCRIPTION OF THE PREFERRED EMBODIMENTS

In view of the above description, reference is now made to FIGS. 1–7, in which a preferred embodiment of the apparatus for checking pulse rate and heart rate according to the present invention is illustrated for assistance in explaining the features thereof.

Figure 1:
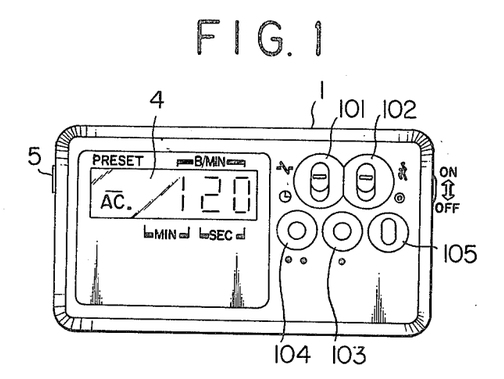
FIG. 1 is a front view showing the measurement unit of a preferred embodiment of the apparatus for checking pulse rate and heart rate according to the present invention.

FIG. 1 shows a front view of a measurement unit used for the apparatus according to the present invention. In the figure, the reference numeral 1 denotes a small-sized rectangular-shaped measurement unit, which includes an indicator unit 4 such as a liquid crystal display on which the measured numerals of pulse rate or heart rate can be legibly displayed. The mark AC (action) in the indicator unit shows that the power supply is turned on, that is, the unit is ready for measurement. The reference numeral 101 denotes a mode selector switch. When this switch is set to the upper side, this measurement unit is in pulse mode for indicating the heart rate or pulse rate; when set to the lower side, the measurement unit is in timer mode for indicating the time. The numeral 102 denotes a set switch. When this switch is set to the upper side, this measurement unit is in run mode for indicating heart rate or pulse rate; when set to the lower side, the measurement unit is in set mode for indicating the upper and lower limits of heart or pulse rate.

The numeral 103 denotes a least significant digit setting switch used in timer mode for presetting a digit representative of from one to nine minutes, and the numeral 104 denotes a most significant digit setting switch for presetting two digits representative of from ten to fifty-nine minutes. The numeral 105 denotes a control switch for storing predetermined upper and lower limits of heart or pulse rate into a microcomputer and for starting the measurement unit as a stopwatch or as a timer.

Therefore, when the mode selector switch 101 is set upward and the set switch 102 is also set upward, the indicator unit 4 made of, for instance, a liquid crystal display, digitally displays the current heart rate or pulse rate.

When the mode selector switch 101 is set upward and the set switch 102 is set downward, the indicator unit 4 displays H indicating the state of being ready to set the upper limit of heart or pulse rate. In this state, when the most significant digit setting switch 104 is kept depressed the two most significant digits are displayed in sequence running from 10 to 19 with an appropriate time interval between each display. When the switch 104 is released, the two digits are set as displayed. Next, when the least significant digit setting switch 103 is kept depressed, the least significant digit is displayed in sequence running from 1 to 9 with an appropriate time delay for each display. When the switch 103 is released, the ones' digit is set as displayed. Now, the setting of the upper limit of heart or pulse rate has been completed. In this embodiment, it is possible to set the upper limit thereof from 100 to 199 per minute. When the control switch 105 is depressed, the preset upper limit digits are stored in the memory, and the indicator unit 4 displays L indicating a state being ready for setting the lower limit of heart or pulse rate. In the same manner as in the upper limit setting, it is possible to preset the lower limit of heart or pulse rate ranging from 80 to 179 per minute. When the control switch 105 is next depressed, the preset lower limit digits are also stored in the memory, and the indicator unit 4 displays H indicating readiness to set the upper limit of heart or pulse rate, where necessary. Next, when the set switch 102 is set upward to run mode, a mark is displayed on the mark AC as $\overline{AC}$, indicating that the upper or lower limit of heart or pulse rate has already been preset. Therefore, if the measured result rise above the upper limit or drops below the lower limit, one of two distinguishable alarm sounds is produced, so that a person engaged in exercise can recognize a condition outside of the preset limits.

When the preset upper or lower limit value needs to be reconfirmed, the mode selector switch 101 is set to the pulse mode and the set switch 102 is set to the set mode, and the upper limit digits are then displayed with the indicator H. Next, when the control switch 105 is depressed, the lower limit digits are displayed with the indicator L.

The following is a description of the use of the measurement unit as a timer: When the mode selector switch 101 is set downward to timer mode and the set switch 102 is also set downward to set mode, the indicator unit 4 displays zero indicating the state of being ready to set a target time. In the same manner as in the upper limit digit setting, it is possible to preset the target time from 1 to 59 minutes by using the most significant digit switch 104 and the least significant digit switch 103. By depressing the control switch 105, the target time is stored in the memory.

Once the target time has been preset, when the set switch 102 is set upward to the run mode and the control switch 105 is depressed, the timer starts to count the time elapsed. And when the time reaches the target time, a buzzer produces an alarm sound indicating zero on the indicator unit.

When the preset time needs to be reconfirmed, the mode selector switch 101 is set to timer mode and the set switch 102 is set to the set mode, and the preset time is displayed. Even if the timer has already started, the timer continues to count. In this case, only when the control switch is depressed, the time is stopped. When the power switch is turned off, the preset timer is released.

The following is a description of the use of the measurement unit as a stopwatch. When the mode selector switch 101 is set downward to timer mode and the set switch 102 upward to run mode, the indicator unit displays zero, indicating the state of being ready to start using it as a stopwatch. In this case, if a preset sign is displayed, the stopwatch cannot function. Therefore, it is necessary to release all preset digits by turning the power switch off once. When the control switch is depressed the first time, the stopwatch starts displaying the count every second; when depressed the second time, the stopwatch stops; when depressed the third time, the stopwatch is reset.

Figure 2:
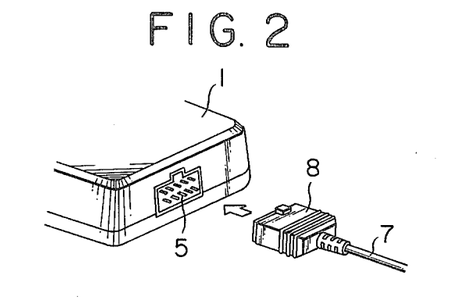
FIG. 2 is a perspective fragmentary view showing the connector provided for the measurement unit for assistance in explaining the connector.

FIG. 2 shows a connector pin 5 provided for the measurement unit 1 and a connector plug 8 to removably connect a heart sensor or a pulse sensor to the measurement unit through a cable 7. The heart sensor or the pulse sensor is connected to the measurement unit 1 freely, according to the state of the person engaged in exercise, by exchanging the respective connector plugs 8.

Figure 3A:
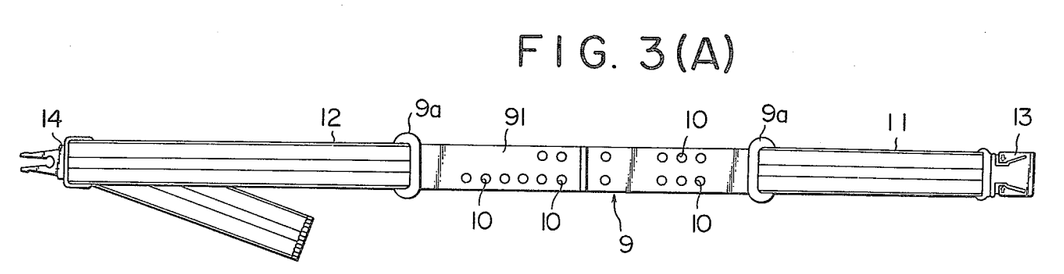
FIG. 3(A) is a front view of the sensor for checking heart rate according to the present invention.
Figure 3B:
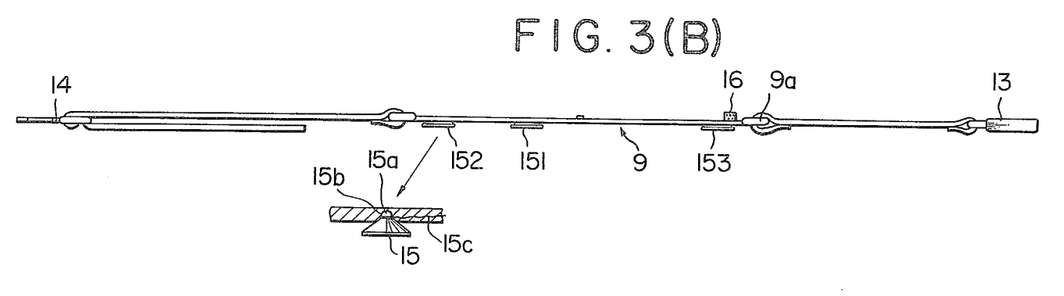
FIG 3(B) is a side view of the sensor for checking heart rate according to the present invention.
Figure 4:
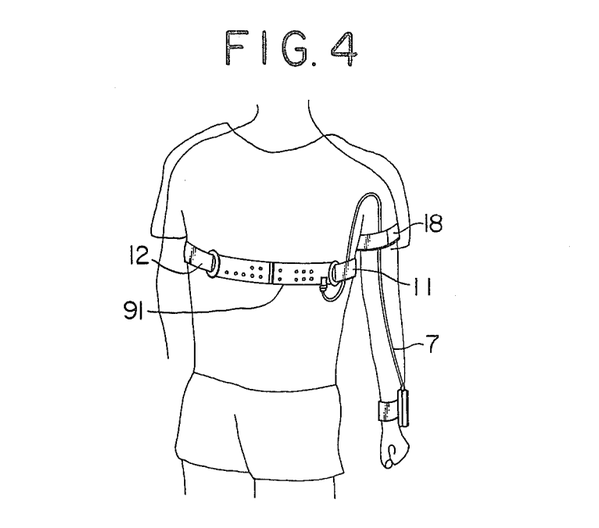
FIG. 4 is a pictorial view illustrating the state where the apparatus for checking heart rate according to the present invention is attached appropriately.

FIGS. 3(A) and (B) show a sensor 9 for checking heart rate. The heart sensor 9 is formed into a strap 91, being made of a flexible resin material such as a silicon rubber. The length of the sensor strap 91 is so designed as to be roughly equal to the chest width, and there are provided a number of holes 10 (cutouts). These holes 10 serve to prevent the rubber-made heart sensor from slipping on the skin and to provide a flow passage for sweat. On both the ends of the sensor strap 91, there are two oval-shaped rings 9a through which cloth belts 11 and 12 are attached. At either end of the cloth belts, a buckle 13 and a clip 14 are connected to adjustably fasten the sensor around the chest of a person in exercise. FIG. 4 shows the state where the heart sensor is attached appropriately. As shown in FIG. 3(B), three circular cone shaped flexible conductive-rubber electrodes 15 are provided on one side of the sensor strap 91. Being made of a conductive rubber, the top 15a of the electrode 15 is implanted or molded integrally with the sensor strap 91. A terminal 15b is provided near the top 15a and a lead wire 15c is connected to this terminal also being molded within the sensor strap 91. The lead wire 15c is connected to a connector 16 attached on the opposite side of the sensor strap 91. The other two electrodes are the same as described above. Therefore by connecting this connector 16 provided on the heart sensor 9 and the connector 5 provided on the side of the measurement unit 1 through a cable 7, it is possible to display the measured heart rate on the indicator unit 4 of the measurement unit 1. In this case, it is preferable to fasten the cable 7 on the arm by using a belt 18, as shown in FIG. 4, especially when heart rate is checked during exercise.

These cone-shaped electrodes 15 are used to directly detect the electrocardiowave voltage generated near the heart. The center electrode 151 is placed roughly over the heart and the other two electrodes 152 and 153 are placed on either side of the chest. Since the electrocardiowave voltage is very low, the differential value between the voltage generated between the electrodes 151 and 152 and the voltage generated between the electrodes 151 and 153 is detected for checking the heart rate, so that the noise can be cancelled for stable detection of the electrocardiowave signal.

Figure 5A:
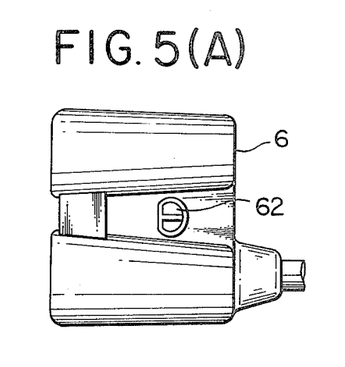
FIG. 5(A) is a top view of the sensor for checking pulse rate according to the present invention.
Figure 5B:
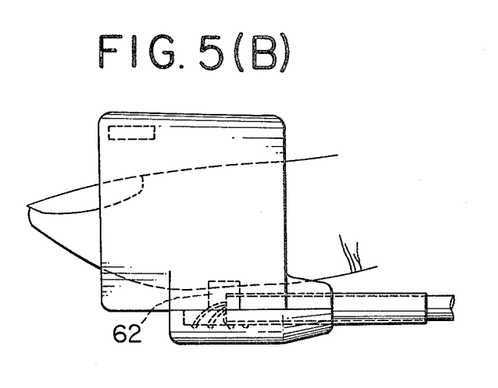
FIG. 5(B) is a side view of the sensor for checking pulse rate according to the present invention.
Figure 5C:
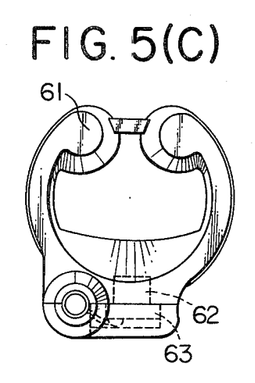
FIG. 5(C) is a cross-sectional view of the sensor for checking pulse rate according to the present invention.
Figure 6:
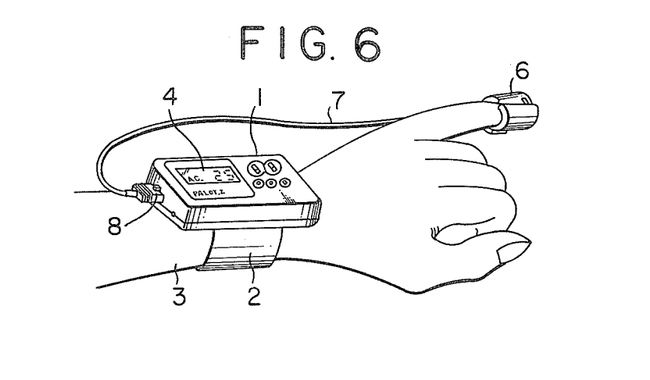
FIG. 6 is a pictorial view showing the apparatus for checking pulse rate according to the present invention attached appropriately.

FIGS. 5(A), (B) and (C) show the sensor for checking pulse rate, and FIG. 6 shows the state in which the measurement unit and the pulse sensor are attached to the hand and the finger tip appropriately. In this case, it is also possible to attach the measurement unit around the waist through a belt.

Being made of a flexible synthetic resin material such as a silicon rubber, the pulse sensor 6 is formed into roughly a cylindrical shape and more particularly a horseshoe-shaped cross section with bulbous lips 61 at either end thereof and with a bridged slit at the top thereof, so that the tip of one appropriate-sized finger can smoothly be fitted into the pulse sensor 6 freely and exactly without applying excessive pressure to the finger. Since there is provided an appropriately-opened slit at the top thereof, it is possible to prevent accumulation of perspiration from the finger skin. A sensor unit 62 is made up of a matching infrared-ray emitting diode and phototransistor fixed onto a base plate 63 molded together at the bottom of the cylindrical pulse sensor, with which the finger pad is in contact whenever the finger is inserted thereinto properly, as depicted in FIG. 5(B). In this embodiment, since noise is usually generated from the finger tip, the pulse sensor diode and transistor are positioned so as to be brought into contact with the finger pad a distance away from the finger tip.

The infrared-ray emitted from the light-emitting diode is reflected from the blood flowing through the capillary vessels under the finger pad and is detected by the light-receiving phototransistor, so that the pulse rate can be detected.

The pulse sensor 6 is removably connected to the measurement unit 1 through the cable 7 and the connector 8.

Therefore, when checking of pulse rate is required, the pulse sensor 6 can be connected to the measurement unit 1; and alternatively, when checking of heart rate is required, the heart sensor 9 can be connected to the measurement unit 1 in place of the pulse sensor 6.

Figure 7:
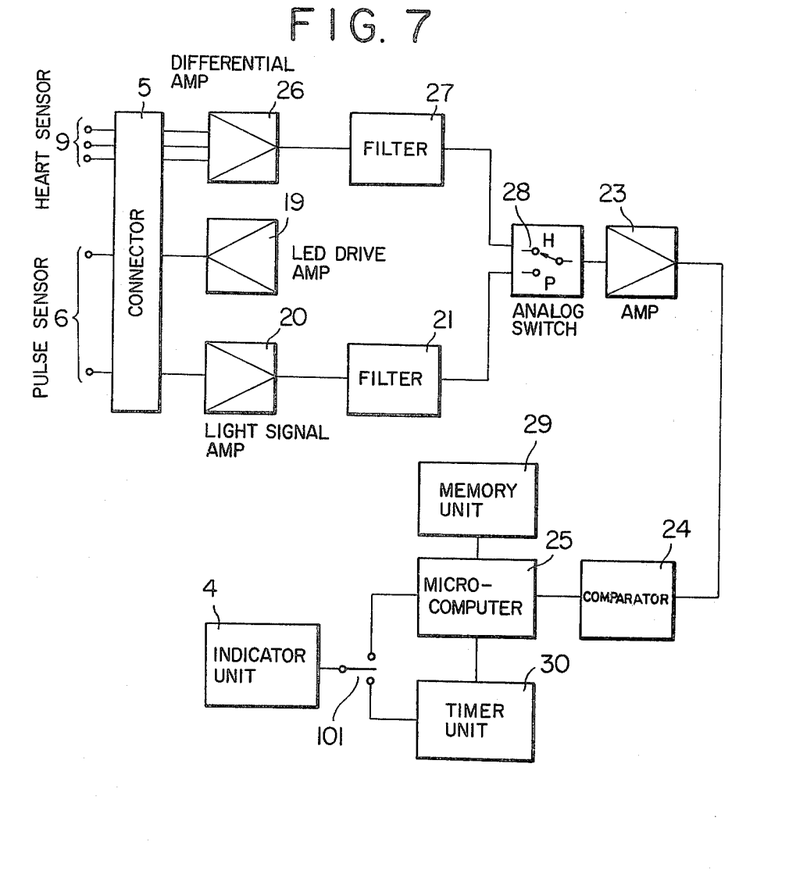
FIG. 7 is a schematic block diagram of a control unit used for the measurement unit according to the present invention.

FIG. 7 shows a schematic block diagram of a control unit used for the measurement unit. The reference numeral 5 denotes a connector to which the above-mentioned heart sensor 9 or pulse sensor 6 is connected.

In the case where the heart sensor 9 is connected to the connector 5, the two electrocardiowave voltages detected by the three electrodes 15 are inputted to a differential amplifier 26 in order to eliminate noise and are next waveform-shaped through a first filter 27. The heart rate signal is then sent into an analog switch 28 (described later in detail), amplified by an amplifier 23, compared with a predetermined level by a comparator 24, and inputted to a microcomputer 25. The microcomputer in conjunction with a memory unit 29 counts the two time intervals between each of three heartbeat pulses and calculates the pulse rate per minute. In this calculation, the microcomputer 25 executes various calculation, comparison, and judgement steps in accordance with programs stored in a read-only memory unit 29 in order to avoid the effect of noise or to ignore an abnormal abrupt fluctuation of heart rate, that is, to only output a relatively stable heart rate to the indicator unit 4 without annoying the person checking the heart rate with this apparatus. The heart rate derived by the microcomputer 25 through appropriate arithmetic operations is lastly displayed on the indicator unit 4, such as a liquid crystal display.

Next, in the case when the pulse sensor 6 is connected to the connector 5, the light-emitting diode is driven by a LED drive amplifier 19. The light reflected from the blood flowing through capillary vessels under the finger pad is detected by the light-receiving phototransistor and is amplified through a light signal amplifier 20 and next waveform-shaped by a second filter 21. Afterward, the pulse rate signal is sent into the analog switch 28, amplified through the amplifier 23, compared with a predetermined level through the comparator 24, and inputted to the microcomputer 25. In the same way as described in the case of the heart sensor, the pulse rate derived by the microcomputer 5 through appropriate arithmetic operations is lastly displayed on an indicator unit 4.

The reference numeral 28 denotes a semiconductor analog switch circuit. When the heart sensor 9 is connected to the connector 5, an input signal is applied from the heart sensor 9 to the input of a semiconductor switching unit of the analog switch 28. The switch circuit connects the first filter 27 to the amplifier 23 in order to conduct the heart rate signal through to the indicator unit 4. On the other hand, when the pulse sensor 6 is connected to the connector 5, another input signal is applied from the pulse sensor 6 to the input of another semiconductor switching unit of the analog switch 28. The switch circuit connects the second filter 21 to the amplifier 23 in order to conduct the pulse rate signal through to the indicator unit 4.

On the other hand, since a timer unit 30 for outputting a train of clock pulses is provided within the control unit so as to operate in cooperation with the microcomputer 25, it is also possible to set the upper and lower pulse or heart rate limits in order to produce an alarm when the measured rate is out of the range, or to use the measurement unit as a stopwatch or a timer unit by additionally providing the mode selector switch 101, set switch 102, least significant digit setting switch 103, most significant digit setting switch 104, and control switch 105. These switches are appropriately connected to the microcomputer 25 for executing necessary processing.

As described above, since the apparatus for checking pulse or heart rates according to the present invention is used as either a pulsimeter or a cardiometer according to need, that is, according to the state when the body is at rest or when the body is in motion, it is possible to obtain accurate pulse or heart rate easily, thus contributing to a further accurate health management.

Further, since the apparatus is small in size, light in weight, and simple in structure, it is possible to attach it at any desired position of the body and to remove it easily.

It will be understood by those skilled in the art that the foregoing description is in terms of preferred embodiments of the present invention wherein various changes and modifications may be made without departing from the spirit and scope of the invention as set forth in the appended claims.

What is claimed is:

1. An apparatus for checking pulse and heart beat rates of a person, which comprises:
    (a) heart beat sensor means for detecting an electrocardiowave and outputting an electrocardiowave voltage signal;
    (b) pulse beat sensor means for detecting a pulse and outputting a pulse signal;
    (c) connector means to which either one of said heart beat sensor means and said pulse beat sensor means is selectively connected;
    (d) analog switch means connected by said connector means to said heart beat sensor means and said pulse beat sensor means;
    (e) microcomputer means connected to said analog switch means, said analog switch means connecting said heart beat sensor means to said microcomputer means when said heart beat sensor means is connected to said connector means and said pulse beat sensor means to said microcomputer means when said pulse beat sensor means is connected to said connector means, said microcomputer means operable for calculating either one of said heart beat rate per minute and said pulse beat rate per minute in response to either of the electrocardiowave voltage signal and the pulse signal; and
    (f) indicator means connected to said microcomputer means for displaying the calculated heart beat rate or pulse beat rate.

2. An apparatus for checking pulse and heart beat rates of a person as set forth in claim 1, wherein said heart beat sensor means comprises:
    (a) a flexible strap so sized as to fit around the person's chest and having a plurality of passage means for preventing accumulation of perspiration when the strap is fitted around the person's chest;
    (b) three flexible circular-cone-shaped electrodes attached to said strap at positions so chosen that when said strap is fitted around the person's chest, a first electrode contacts the person's chest at a point directly opposing the person's heart and the second and third electrodes contact the person's chest at points on opposite sides of the person's heart, respectively;
    (c) a connector attached to said strap for electrically connecting each of said electrodes to said connector means of the apparatus;
    (d) three wires molded into said strap electrically connecting each of said three electrodes to said connector respectively; and
    (e) a pair of cloth belts each having first and second ends, one of said belts including a buckle at the first end thereof and the other of said belts including a clip at the first end thereof, each of said belts being connected at the second ends thereof to opposing ends of said strap for adjustably fastening said heart beat sensor means around the person's chest.

3. An apparatus for checking pulse and heart beat rates of a person as set forth in claim 1, wherein said pulse beat sensor means comprises:

(a) a flexible ring of variable diameter and so sized as to fit around the person's finger at a point remote from the tip thereof, said ring being open at both ends to allow egress of perspiration;

(b) a sensor unit including an infrared light-emitting diode and an infrared phototransistor, said sensor unit being molded within said ring at a position exposed to the person's finger when said pulse beat sensor means is in use so that the phototransistor detects and outputs a pulse signal indicative of the intensity of the infrared light emitted from the light emitting diode and reflected from the person's finger; and (c) a connector attached to said ring electrically connecting said sensor unit to said connector means of the apparatus.

4. Apparatus for checking and displaying cardiac rates comprising:

(a) first sensor means for detecting an electrocardiowave and outputting an electrocardiowave voltage signal;

(b) second sensor means for detecting a pulse beat and outputting a pulse signal;

(c) electric circuit means comprising:

(i) first circuit means for filtering said electrocardiowave signal;

(ii) second circuit means for filtering said pulse signal; and (iii) computing and display means for selectively computing heart beat rate from said filtered electrocardiowave voltage signal and a pulse rate from said filtered pulse signal and for displaying the selectively computed rate;

(d) common connector means for connecting one of said first and second sensor means to said electrical circuit means; and (e) switching means for selectively connecting said first circuit means to said computing and display means when said first sensor means is connected to said common connector means and for connecting said second circuit means to said computing and display means when said second sensor means is connected to said common connector means;

whereby an appropriate one of said heart beat rate or said pulse rate is computed and displayed when either of said first or second sensor means is connected to said common connector means.

5. Apparatus for checking and displaying cardiac rates as recited in claim 4 wherein said switching means is responsive to signals received via said common connector means from said first and second sensor means for connecting said first or second circuit means to said computing and display means.

* * * * *